(12) United States Patent
Picollet-Dahan et al.

(10) Patent No.: US 7,494,622 B2
(45) Date of Patent: Feb. 24, 2009

(54) DEVICE FOR MEASURING THE ELECTRICAL ACTIVITY OF BIOLOGICAL ELEMENTS AND ITS APPLICATIONS

(75) Inventors: Nathalie Picollet-Dahan, La Ferriere (FR); Patrice Caillat, Echirolles (FR); Frederic Revol-Cavalier, Seyssins (FR); Francois Chatelain, Voreppe (FR); Fabien Sauter, Seyssinet-Pariset (FR)

(73) Assignee: Commissariat a l'Energie Atomique, Paris (FR)

( * ) Notice: Subject to any disclaimer, the term of this patent is extended or adjusted under 35 U.S.C. 154(b) by 900 days.

(21) Appl. No.: 10/522,599

(22) PCT Filed: Aug. 28, 2003

(86) PCT No.: PCT/EP03/15044

§ 371 (c)(1),
(2), (4) Date: Jan. 26, 2005

(87) PCT Pub. No.: WO2004/038409

PCT Pub. Date: May 6, 2004

(65) Prior Publication Data

US 2006/0163063 A1   Jul. 27, 2006

(30) Foreign Application Priority Data

Aug. 28, 2002   (FR) .................................. 02 10663

(51) Int. Cl.
*G01N 27/00* (2006.01)

(52) U.S. Cl. .................. 422/82.01; 422/82.02; 422/102; 324/691; 324/692

(58) Field of Classification Search .............. 422/82.01, 422/82.02, 102; 436/149, 150; 374/439, 374/443–446, 449, 450, 691, 692; 435/287.1, 435/288.4; 204/400, 403.01, 412
See application file for complete search history.

(56) References Cited

U.S. PATENT DOCUMENTS 4,894,343 A * 1/1990 Tanaka et al. ............ 435/285.2

(Continued)

FOREIGN PATENT DOCUMENTS

WO   96/13721   5/1996

(Continued)

OTHER PUBLICATIONS

Hamill, O.P. et al. "Improved Patch-Clamp Techniques for High-Resolution Current Recording from Cells and Cell-Free Membrane Patches", Pfluegers Arch, vol. 391, pp. 85-100.

*Primary Examiner*—Jill Warden
*Assistant Examiner*—Dwayne K Handy
(74) *Attorney, Agent, or Firm*—Oblon, Spivak, McClelland, Maier & Neustadt, P.C.

(57) ABSTRACT

A device for measuring electrical activity of biological elements, including a substrate that has lower and upper faces and at least one through opening, the opening being delimited by a set of walls. Two plates are placed on either side of the lower and upper faces of the substrate and delimit, with the set of walls, a chamber. Each of the plates is provided, on its face lying opposite the substrate, with at least one electrode facing the opening in the substrate. Each of the plates further has at least one channel that starts inside the chamber and connects the chamber to the outside of the device, and the chamber communicates with the outside of the device only through the channels.

31 Claims, 5 Drawing Sheets

U.S. PATENT DOCUMENTS

| | | | |
|---|---|---|---|
| 5,506,141 A * | 4/1996 | Weinreb et al. | 435/309.1 |
| 5,643,742 A | 7/1997 | Malin et al. | |
| 6,315,940 B1 | 11/2001 | Nisch et al. | |
| 6,776,896 B1 * | 8/2004 | Osipchuk | 205/777.5 |
| 6,932,893 B2 * | 8/2005 | Bech et al. | 204/403.01 |
| 6,984,297 B2 * | 1/2006 | Nisch et al. | 204/403.01 |
| 6,989,089 B2 * | 1/2006 | Nisch et al. | 205/777.5 |
| 7,169,609 B2 * | 1/2007 | Negulescu et al. | 435/395 |

FOREIGN PATENT DOCUMENTS

| | | |
|---|---|---|
| WO | 97/16726 | 5/1997 |
| WO | 99/31503 | 6/1999 |
| WO | 99/66329 | 12/1999 |
| WO | 00/25121 | 5/2000 |
| WO | 01/25769 | 4/2001 |
| WO | 01/59447 | 8/2001 |
| WO | 01/71349 | 9/2001 |

* cited by examiner

DEVICE FOR MEASURING THE ELECTRICAL ACTIVITY OF BIOLOGICAL ELEMENTS AND ITS APPLICATIONS

FIELD OF THE INVENTION

The present invention relates to a device for measuring the electrical activity of one or more biological elements, and more especially to a device that makes it possible to measure the electrical activity of a plurality of biological elements in parallel.

It also relates to the applications of this device.

In the above and in what follows, the term "biological element" is understood to mean any natural or artificial element at least part of which is formed from a biological membrane or reproduces the structural and/or functional characteristics of a biological membrane.

Thus, it may be a whole biological cell or a biological cell organelle of the type comprising a vacuole, Golgi apparatus, mitochondria, endoplasmic reticulum, lysosome, etc., a biological membrane fragment, possibly furnished with cytosolic components, an artificial lipid bilayer, such as a phosphatidyl choline or phosphatidyl glycerol film, said bilayer being provided with one or more protein pores, or else a biomimetic membrane.

The genesis and transmission of the electrical signals present in biological cells depend on transmembrane proteins that form pores in the thickness of the plasma membranes and ensure that ions ($Na^+$, $Ca^{++}$, $K^+$ and $Cl^-$) pass through these membranes, hence their name "ion channels". Most of these ion channels open in response to a specific disruption of the membrane in which they are located, which disruption may be associated either with a change in the electrical potential of this membrane (they are then called voltage-sensitive or voltage-dependent channels) or with the binding of a ligand to a membrane receptor (they are then called receptor channels).

At the present time it is known that the dysfunctioning of certain ion channels is involved in major pathologies, among which mention may be made of epilepsy, myotonias, cerebrospinal ataxia, high blood pressure, cardiac insufficiency, arrythmias such as ventricular quadriarrythmia syndrome and Jervell and Lange-Nielsen syndrome, cystic fibrosis, diabetes and certain kidney disorders such as Bartter's and Gritelman's syndromes and pseudohypoaldosteronism type 1 (PHA-1). Likewise, certain ion channels appear to be involved in the genesis and regulation of nociceptive messages that are the cause of acute pain and chronic pain.

The device according to the invention may therefore constitute a tool of choice for the pharmaceutical research and especially for carrying out studies with a view to better understanding the mechanisms responsible at the cell level for disorders associated with an ion channel dysfunction, to identifying the sites and modes of action of drugs already recognized as being effective in the treatment of these disorders and, from this, to developing new drugs that are more active and more specific than those already available.

In particular, the device according to the invention may be applicable in the field of pharmacology, for studying antidotes and drugs against certain poisons or venoms (for example, scorpion venom), for the medium- or high-throughput screening of molecules that have ion channels as targets and may consequently be of therapeutic value, or of candidate drugs so as to evaluate their effects and/or their toxicity, and also in the field of pharmacovigilance.

It may also be used for the diagnosis of pathologies associated with an ion channel dysfunction.

Moreover, ion channels of the receptor-channel type may be used as "channel sensors" in so far as any modification of their electrical activity reflects the presence of a molecule that they are capable of detecting. Consequently, the device according to the invention may also be used in the environmental field, for example for detecting pollutants, in industries that carry out quality control checks on their manufacturing lines and on the products that are output thereby, such as the agri-foodstuffs, pharmaceutical and cosmetic industries, and also in all other sectors where it is standard practice to carry out toxicological analysis.

The device according to the invention may still be used for many other purposes such as, for example, for detecting living cells or cells having their membrane integrity preserved or, on the contrary, for detecting dead cells or cells having lost their membrane integrity, for detecting the release of substances from cells by exocytosis, for measuring a variation of membrane capacitance resulting from the fusion of a cell with another cell or with a vesicle, for stimulating cells, for studying the intracellular activity of a cellular network, tissue or co-culture, for studying the response of cells to an electrical stimulation applied to another cells, or even for studying mechanical-sensitive ion channels with the view to providing "mechanical" sensors.

PRIOR ART

It was in 1981 that Neher and Sakmann developed the technique for studying ion channels that is still the most effective today, namely the "patch-clamp" technique (Hamill et al., Pflügers Arch., 1981, 391:85-100) [1]. This technique makes it possible to check ("clamp") the transmembrane electrical potential differences within a plasma membrane fragment ("patch") or within a whole cell and thus obtain, directly, the ion fluxes through the ion channels of this membrane patch or of this cell.

In practice, the technique consists in applying a glass micropipette to the plasma membrane of a cell and in creating, by suction in the micropipette, a seal having a high resistance, of the order of 1 gigaohm usually named "gigaseal", between the end of this micropipette and the membrane patch to which the micropipette is attached ("cell-attached" configuration), it being possible to continue applying suction until the opening of this membrane patch is obtained ("whole-cell" configuration). The membrane patch can then be isolated from the rest of the cell by mechanical excision ("inside-out" or "outside-out" configurations).

It is then possible, by applying a constant electrical voltage to the membrane patch or to the cell and by recording the variations in this voltage, to measure the electrical activity resulting from a change of state (opening or closing) of the ion channels on the single isolated membrane patch in cell-attached or excised configuration, or on the entire cell membrane in whole-cell configuration.

Although there is no question that the patch-clamp technique, because of its sensitivity, has allowed research to make considerable progress in the understanding of ion channels and has given the pharmaceutical industry a tool for screening molecules that can act on ion channels, it turns out that this technique is not completely satisfactory.

This is because, in the first place, it has the drawback of being very sensitive to the electrical noise and vibrations coming from the surrounding medium and, consequently, of requiring a relatively substantial infrastructure (anti-vibration tables, Faraday cages, etc.) designed to neutralize the interfering effects of such noise and vibration.

Moreover, it is an entirely manual method, which is quite cumbersome to implement, especially because the glass micropipettes that it uses must be prepared, before each measurement, by the drawing and machining of capillaries, and which requires the presence of a highly trained experimenter, in particular for suitably positioning these micropipettes and for obtaining the gigaseal, since the suction that allows this gigaseal to be formed is applied by mouth.

In addition, the number of specimens that can be examined per time unit is quite small and the percentage of failures high. As an indication, an experimenter experienced in the patch-clamp technique can at best make twenty measurements per day.

It will consequently be understood that the patch-clamp technique cannot be used either for medium- or high-throughput pharmacological screening, as desired by pharmaceutical research, or for routine tests as is required for the use of ion channels as sensors.

The limitations of the patch-clamp technique as proposed by Neher and Sakmann, coupled with the fact that the advances in genome research and in information technologies have demonstrated both the great diversity and great complexity of ion channels, have led to the emergence, in recent years, of many attempts to improve this technique.

Specifically, two approaches have been explored: firstly, that aiming to automate the measurements, while still using the same electrodes as in the original technique (glass micropipettes), and, secondly, that aiming to carry out the measurements on electronic chips.

Thus, for example
- NEUROSEARCH has developed an automatic cell recognition and measurement apparatus for measuring eight individual cells in separate chambers. This apparatus, which is desclosed in WO-A-96/13721 [2], makes it possible to carry out electrical activity measurements with high efficiency. However, since the cells are cultured and "patched" on solid surfaces, it requires very precise selection of the cells and the use of a system for positioning the pipette used to establish the high-resistance seal that is able to prevent the glass recording electrodes from breaking.
- SOPHION BIOSCIENCES has developed a standard substrate allowing electrical events within biological membranes to be recorded. This substrate, which is disclosed in WO-A-01/25769 [3], has a plurality of sites, of square cross section, into which electrodes are integrated. However, it turns out that in use, these sites are ill-suited to obtaining a high-resistance seal with the cells.
- CENES has introduced a novel patch-clamp system for measuring the electrical activity of whole cells. This system, which is disclosed in WO-A-01/71349 [4], involves suspending the cells in a liquid medium and in presenting them to an electrode, at an air/liquid interface in a glass capillary. This system has the advantage of eliminating the problems caused by the vibrations emitted by the surrounding medium and of not requiring very precise positioning of the electrode. However, it does not allow measurements to be conducted in parallel.
- This last company has also proposed, in WO-A-00/66329 [5], a porous or perforated substrate, arranged in wells and on either side of which there are electrodes. The cells are positioned on this substrate in the form of a cell layer, so that it does not allow measurements on individual cells to be carried out.
- CYTION has disclosed in WO-A-99/31503 [6] a device for positioning cells, which has the feature of including only a single integrated measurement site per chip and of having no structure allowing confinement of the cells. As a result, there is a not insignificant risk of the cells spreading and of several cells being present on the same site.
- AXON is currently working on a draft version of a device that uses plane silicone elastomer electrodes proposed by Yale University in its International Application WO-A-01/59447 [7]. The first tests have shown that this device still requires substantial improvements to be made.
- Lastly, devices that are intended to convert ion movements produced by ion channels into alternating electrical currents able to be detected and measured are described in WO-A-00/25121 [8]. These devices include a substrate provided with a hole in which an ion channel or a membrane fragment comprising one or more ion channels is incorporated before using, and are fully unsuitable for measuring the electrical activity of whole biological elements such as cells or cell organelles.

The inventors were therefore given the objective of providing a device that can measure the electrical activity of biological elements, and especially of cells, using the patch-clamp technique, so as to benefit from the advantages of this technique, in particular in terms of sensitivity, but without, however, having the drawbacks thereof, in such a way that it is possible with this device to make simultaneous measurements of cell electrical activity at a rate and with a reliability that will especially permit it to be used for the medium- and high-throughput screening of potentially therapeutically useful substances or for carrying out routine tests, in particular diagnostic or toxicity tests.

The inventors were also set the objective of providing a device which, while still having these advantages, is satisfactory from the manufacturing cost and operating cost standpoints.

SUMMARY OF THE INVENTION

These objectives are achieved by the present invention, which proposes a device for measuring the electrical activity of at least one biological element.

This device comprises a substantially plane substrate, which has a lower face and an upper face and which has at least one through opening for housing the biological element, said opening being delimited by a set of walls, and is characterized in that:
- it comprises two substantially plane plates that are placed on either side of the lower and upper faces of the substrate and that delimit with said set of walls a chamber which is filled, when the device is being used, with a liquid medium;
- each of the plates is provided, on its face lying opposite the substrate, with at least an electrode facing the opening in the substrate;
- each of the plates further has at least one channel that starts inside the chamber and connects the latter to the outside of the device; and
- the chamber communicates with the outside of the device only through said channels.

Thus, the device according to the invention comprises, for each biological element whose electrical activity it is desired to measure:
- a chamber that is designed to be filled with a liquid medium within which the biological element is intended to bathe in a housing provided for this purpose, said liquid medium serving to ensure conduction of an electric current and the survival of the biological element, if the latter is a living element;

a pair of electrodes that are distributed over two plates, one of which forms the top of the chamber while the other forms its base, and that face the housing for the biological element, these electrodes having the function of applying an electrical voltage to said biological element and of recording the variations in this voltage resulting from a change of state (opening or closing) of its ion channels; and at least two channels that connect the inside of the chamber with the outside of the device, one of which starts at the base of the chamber and is intended to produce a high-resistance seal between the biological element and its housing, by creating a vacuum in this chamber, whereas the other starts at the top of the chamber and is intended for introducing substances into this chamber and/or removing these substances out of said chamber.

According to a first advantageous arrangement of the invention, the opening in the substrate comprises three coaxial parts, namely an upper part, a central part and a lower part, the upper and central parts forming a cup for housing the biological element, whereas the lower part forms a reservoir for housing a volume of liquid medium sufficient to create therein, by suction, a vacuum suitable for forming a high-resistance seal between said cup and the biological element.

As used herein, the term "high-resistance seal" refers to a seal having a resistance of at least one hundred megaohms and advantageously of one gigaohm or above.

Preferably, the cup for housing the biological element (which for convenience will be denoted, hereafter, only by the term "cup") has the shape of a funnel, the frustoconical part of which corresponds to the upper part of the opening in the substrate and serves as a receptacle for the biological element and the cylindrical part of which corresponds to the central part of this opening and serves for providing the high-resistance seal between this element and said cup.

This shape of cup, in the form of a funnel, has in fact proved to be particularly suitable for confining the biological element, for respecting its form and its integrity, especially when it is a biological cell, for ensuring its deformation or the deformation of its membrane during the creation of a vacuum in the subjacent reservoir and, consequently, for allowing the high-resistance seal to be obtained.

According to the invention, the dimensions of the frustoconical part of the cup serving as receptacle for the biological element are, preferably, matched to the dimensions of this element, thereby making it possible to further improve its confinement and to obtain the high-resistance seal.

Thus, for example, when the biological element is a cell of conventional size, that is to say from around 10 to 30 microns in diameter (lymphocyte, CHO cell, Hela cell, HEK cell, . . . ), the frustoconical part of the cup—which corresponds to the upper part of the opening in the substrate—preferably has its largest diameter between 20 and 100 microns and its smallest diameter between 10 and 30 microns and has a height of between 10 and 50 microns, whereas the cylindrical part of this cup—which corresponds to the central part of the opening in the substrate—preferably has a diameter of between 0.1 and 3 microns and a height of 100 microns or less.

As a variant, when the biological element is a large cell, that is to say one measuring around 0.7 to 1 mm in diameter, as is the case with a xenopus ovocyte, the frustoconical part of the cup preferably has its largest diameter between 500 microns and 1.5 mm and its smallest diameter between 200 and 600 microns and has a height of between 300 microns and 10 mm, whereas the cylindrical part of this cup preferably has a diameter of between 0.1 and 3 microns and a height of 100 microns or less.

In all cases, the lower part of the opening in the substrate is preferably cylindrical and advantageously measures between 10 and 100 microns in diameter for a height of 300 to 700 microns.

According to another advantageous arrangement of the device according to the invention, the substrate is made of one or more micromachinable materials, micromachining being a technique that is particularly well suited to producing openings with dimensions ranging from one tenth of a micron to a few hundred microns.

Preferably, the substrate is based on silicon and is formed from two silicon wafers that are placed on either side of an intermediate membrane which they are fastened to, which intermediate membrane may be made of an insulating material, compatible with microtechnology techniques, or of a silicon wafer coated on its various faces by an insulating material when it is desired to strengthen said intermediate membrane. The insulating material may be a mineral material, such as an oxide (for example, $SiO_2$) or a nitride (for example, $Si_3N_4$), or an organic material (for example, a polyimide).

In this situation, the upper part of the opening in the substrate (i.e. the frustoconical part of the cup) is delimited by the wall of a through recess made in one of the two silicon wafers that are placed on either side of the intermediate membrane, whereas the lower part of the opening in the substrate (i.e. the reservoir) is delimited by the wall of a through recess made in the other of said silicon wafers.

Between the upper and lower parts of the opening in the substrate, the central part of this opening (i.e. the cylindrical part of the cup) is, in a simplest embodiment of the device, delimited by the wall of a through recess made in the intermediate membrane.

However, it is also possible that the central part of the opening in the substrate forms a kind of micropipette that extends into the upper part of the opening in the substrate, and is delimited at the same time by a first cylindrical wall corresponding to the wall of a through recess made in the intermediate membrane and by a second cylindrical wall protruding from the first cylindrical wall towards the upper face of the substrate. Such a configuration, the dimensions of which may be perfectly controlled, may easily be achieved by the Silicon-on-Substrate (SOI) technology, the second cylindrical wall having preferably a height of between 1 and 30 microns for a diameter of between a few tenth of a micron and a few microns.

Quite obviously, micromachinable materials other than those previously cited may be perfectly usable for producing the substrate, such as glass or plastics.

According to yet another advantageous arrangement of the device according to the invention, the upper face of the substrate is covered with a film that is made of a biocompatible and optionally flexible material, and is provided with at least one through opening, this opening being coaxial with the upper part of the subjacent opening in the substrate, with the same geometry as it but with a larger cross section.

This arrangement, which is particularly useful when it is desired to measure the electrical activity of large cells, makes it possible not only to optimize the confinement of this type of cell but also to reduce the thickness of that part of the substrate made of the micromachinable material(s) and thus lower the manufacturing cost of this substrate compared with what it would be it if were entirely made of micromachinable material(s) such as silicon.

Preferably, the opening in the film covering the upper face of the substrate is frustoconical and has its largest diameter between 500 microns and 1.5 mm and its smallest diameter between 200 and 600 microns and has a height of between 300 microns and 1 mm.

Advantageously, this film is made by moulding, so that its manufacturing cost is low enough for it to be replaced with a fresh film each time the device is used, and is therefore made of a material capable of being moulded, such as a thermoplastic of the polytetrafluoroethylene (PTFE) type, or a silicone elastomer, such as a polydimethylsiloxane (PDMS).

Depending on the nature of the materials of which the film and the substrate are made, the film may be held in place on the substrate either by bonding or by an adhesion effect under the effect of pressure.

According to the invention, the plates lying on either side of the lower and upper faces of the substrate, which may be identical or different, are preferably made of an insulating material, for example a glass-epoxy, whereas the electrodes carried by these plates are preferably plane electrodes.

The latter may especially be Ag/AgCl⁻ contacts, but contacts consisting of other oxidation-reduction pairs may also be used, such as Pt/PtCl⁻ pairs.

In all cases, the electrodes are designed to be connected, after the various elements of the device have been assembled, to a circuit for supplying electrical power and for measuring an electrical quantity.

According to yet another advantageous arrangement of the invention, the plate lying opposite the upper face of the substrate has two channels, namely a channel for introducing substances into the chamber and a channel for removing these substances from this chamber, whereas the plate lying opposite the lower face of the substrate has only one channel, said channel being intended to produce the high-resistance seal.

The channels for introducing and removing substances are designed to be respectively connected, momentarily or permanently, to capillaries that allow them to be respectively connected to an automatic or manual liquid delivery system and to an automatic or manual liquid suction system, these two systems being able to be connected to each other so as to recirculate said substances into the chamber.

The channel for producing the high-resistance seal is designed to be connected, momentarily or permanently, to a capillary that allows it to be connected to a liquid suction system.

According to the invention, these various channels may connect the chamber to the outside of the device by passing through the thickness of the plate in which they are located.

As a variant, they may also connect the chamber to the outside of the device by circulating within the plate in which they are located, substantially parallel to the faces of this plate, until reaching one of the edges of said plate.

According to a preferred arrangement of the device according to the invention, the opening in the substrate, the electrodes and the channel of the plate lying opposite the lower face of the substrate are coaxial, this arrangement making it possible in particular to optimize the creation of the high-resistance seal between the cup and the biological element, the application to the latter of the electrical voltage needed to measure its electrical activity, the recording of the variations of this voltage and, consequently, the quality of the measurements thus made.

According to another preferred arrangement of the device according to the invention, the latter comprises means for sealing the chamber, which means also serve for damping the electrical noise and the vibrations emanating from the surrounding medium, and which will for convenience be denoted hereafter only by the term "sealing means".

These sealing means preferably consist of a first gasket, that is inserted between the substrate and the plate lying opposite the lower face of this substrate, and of a second gasket, which may or may not be identical to the previous one, that is inserted between the substrate and the plate lying opposite the upper face of this substrate, each of these gaskets being provided with at least one perforation which is arranged and dimensioned so as to circumscribe the electrode on the plate with which it is in contact.

Advantageously, these gaskets are made of a material which, apart from being impermeable to liquids, is flexible, slightly compressible and capable of being moulded so that it can be produced by moulding, thereby making it possible, on the one hand, to adapt them perfectly to the configuration of the substrate and, on the other hand, to manufacture them at a low enough cost for it to be possible to replace them with fresh gaskets each time the device is used. Such a material is, for example, an elastomer like a silicone elastomer, such as a polydimethylsiloxane.

According to yet another preferred arrangement, the substrate, the plates lying on either side of the lower and upper faces of this substrate and the sealing means are modules that are assembled in a removable manner.

In this case, the device according to the invention advantageously includes means for holding these modules in place in the assembled condition.

These holding means may be means fastened to the plates lying on either side of the lower and upper faces of the substrate and cooperate in order to removably fix these plates to each other, such as hinges, slideways or screwing means. They may also be means that are independent of these plates and that fit onto the edges of the stack formed by the various modules.

Assembly of the modules, and more particularly alignment of the axes of the openings in the substrate, of the electrodes carried by the plates lying on either side of the lower and upper faces of this substrate and of the perforations in the sealing means, may be facilitated by the presence, especially on said plates, of mechanical guiding means (alignment studs, corner grooves, etc.), optical guiding means (optical fibers passing through preformed holes), or other guiding means.

According to the invention, the device preferably allows the electrical activity of several biological elements to be measured in parallel, in which case:

the substrate has a number of identical through openings uniformly spaced apart;

the plates lying on either side of the lower and upper faces of this substrate are printed circuits that are each provided with as many electrodes as the substrate has through openings;

the plate lying opposite the lower face of the substrate has at least as many channels as the substrate has through openings; and the plate lying opposite the upper face of the substrate has at least as many channels for introducing substances and at least as many channels for removing substances as the substrate has through openings;

said substrate and its through openings, said plates, said electrodes and said channels being as defined above.

According to a preferred embodiment of this device, the latter also includes two identical gaskets, each provided with as many perforations as the substrate has through openings, these gaskets and these perforations being as defined above.

Moreover, according to this preferred embodiment, the device also includes two identical clamps that fit over the edges of the stack formed by the substrate, the plates lying on either side of the lower and upper faces of this substrate and the gaskets.

This being the case, the device according to the invention, although comprising seven elements, is composed of five different modules that can be assembled and disassembled at will, the substrate corresponding to a first module, the plates lying on either side of the lower and upper faces of the substrate corresponding to a second and to a third module respectively, the gaskets corresponding to two examples of a fourth module, while the clamps correspond to two examples of a fifth module.

The device according to the invention has many advantages.

This is because, while still allowing cell electrical activity measurements to be made according to the principles of the patch-clamp technique, it considerably simplifies the implementation of this technique:

firstly, by eliminating the operations of preparing glass micropipettes and of handling these micropipettes, the mouth suction operation needed to obtain the gigaseal, the need to use a microscope and equipment suitable for preventing, or at the very least limiting, any interference due to electrical noise and vibrations emitted in the surrounding medium; and secondly, by offering the possibility of automating all or part of these electrical activity measurements, and especially the formation of the high-resistance seal, the delivery of substances into chambers that are independent of one another, the application of the electrical voltage and the recording of the variations in this voltage, by placing the suction and substance delivery systems and the circuit for supplying electrical power and for measuring an electrical quantity under the control of a computer system.

It follows that the device according to the invention makes the patch-clamp technique available to laboratories and users that have no experience in this field. It also follows that the device allows cell electrical activity measurements to be made with a very satisfactory level of efficiency, while guaranteeing reliability, and especially reproducibility, of these measurements.

Moreover, it offers great flexibility of use in so far as it allows electrical activity measurements to be made both on a plurality of simultaneously treated cells and on a single cell, in cell-attached configuration just as well as in whole-cell configuration, and, when the measurements are conducted in parallel, on several cells, using parameters that may be different from one cell to another. Thus, for example, the survival medium, the substance to be tested or detected, the concentration of this substance and the electrical voltage may differ from one cell to another.

In addition, it may receive, apart from whole cells, either biological cell organelles or fragments of biological membranes possibly furnished with cytosolic components, or artificial lipid bilayers, or else biomimetic membranes.

This operating flexibility is further enhanced when the device according to the invention is a modular system, since, in this case, the various modules may be replaced, or on the contrary reused, from one measurement to another or from one series of measurements to another.

Finally, it can be manufactured very inexpensively, especially when it is in the form of a modular system since, in this case, its manufacture does not include an assembly operation nor an operation to check the quality of this assembly. Similarly, the operating costs of such a device may be very advantageous in so far as it is possible to replace some of the modules of which it is composed, either because they are intended to be used only once, or because they have become damaged, while keeping the other ones.

Taking into account the foregoing, the device according to the invention is capable of constituting a tool of choice for:
screening molecules for therapeutic purposes;
diagnosing pathologies associated with an ion channel dysfunction;
detecting toxic substances, whether in the environmental field or in the agri-foodstuffs, pharmaceutical or cosmetic industries;
detecting living cells or cells having their membrane integrity preserved or, on the contrary, detecting dead cells or cells having lost their membrane integrity;
detecting the release of substances from cells by exocytosis;
measuring a variation of membrane capacitance resulting from the fusion of a cell with another cell or with a vesicle;
stimulating cells such as neurons with a view, for example, to studying or to promoting, or even to speeding-up, the neuronal regeneration, new growth or plasticity;
studying the intracellular activity of a cellular network, of a (organotypical) tissue or of a cellular co-culture;
studying the response of cells A to an electrical stimulation applied to cells B; or even
studying mechanical-sensitive ion channels with the view to providing "mechanical" sensors.

Apart from the above arrangements, the invention includes still further arrangements that will become apparent from the rest of the description that follows, that relates to embodiments of a device according to the invention, and that is given by way of illustration but implying no limitation, with reference to the appended drawings.

DETAILED DESCRIPTION OF THE EMBODIMENTS

Figure 1:
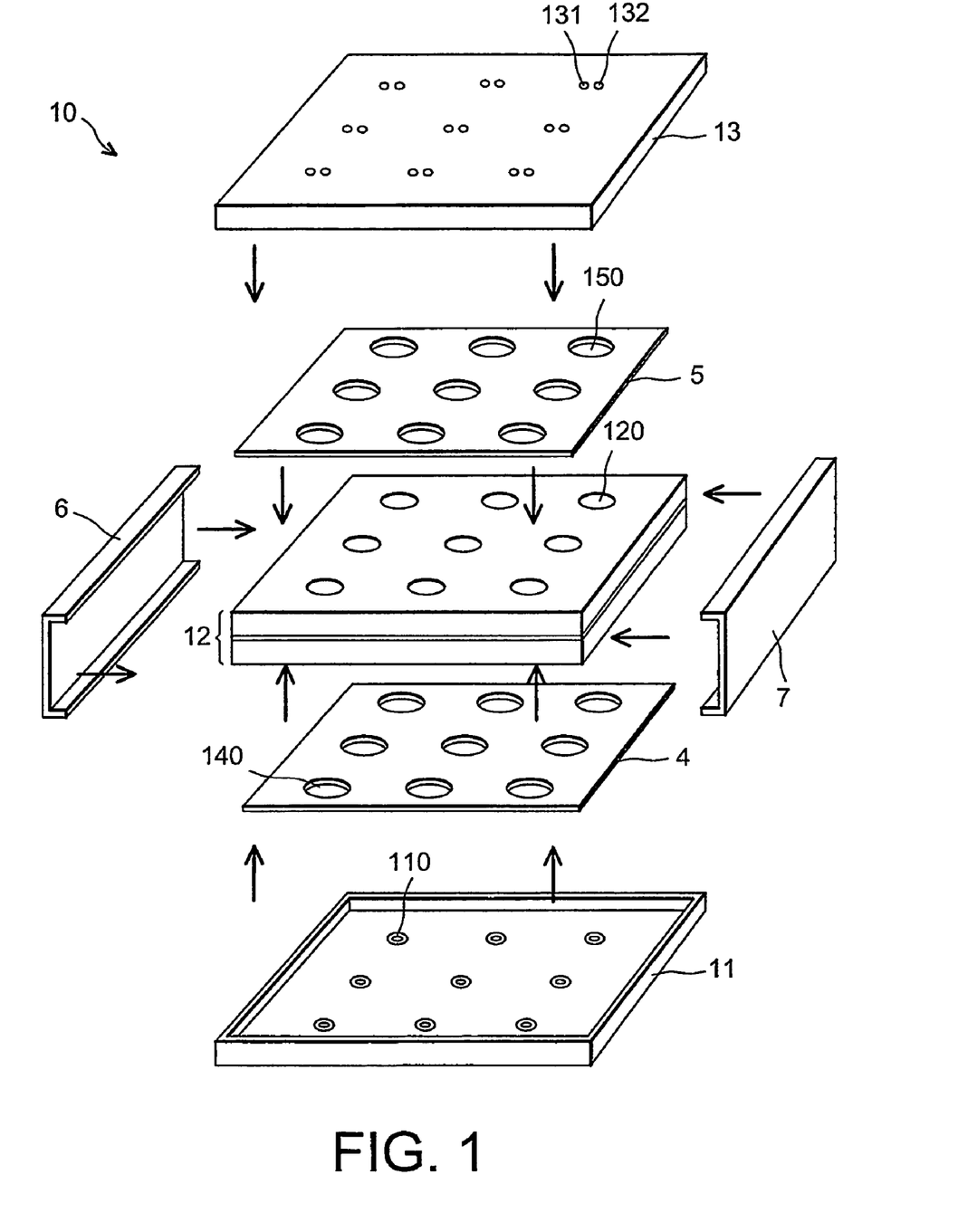
FIG. 1 is a schematic representation of a device according to the invention, seen in exploded perspective, in an embodiment designed for the electrical activity of nine biological cells to be measured in parallel.
Figure 2:
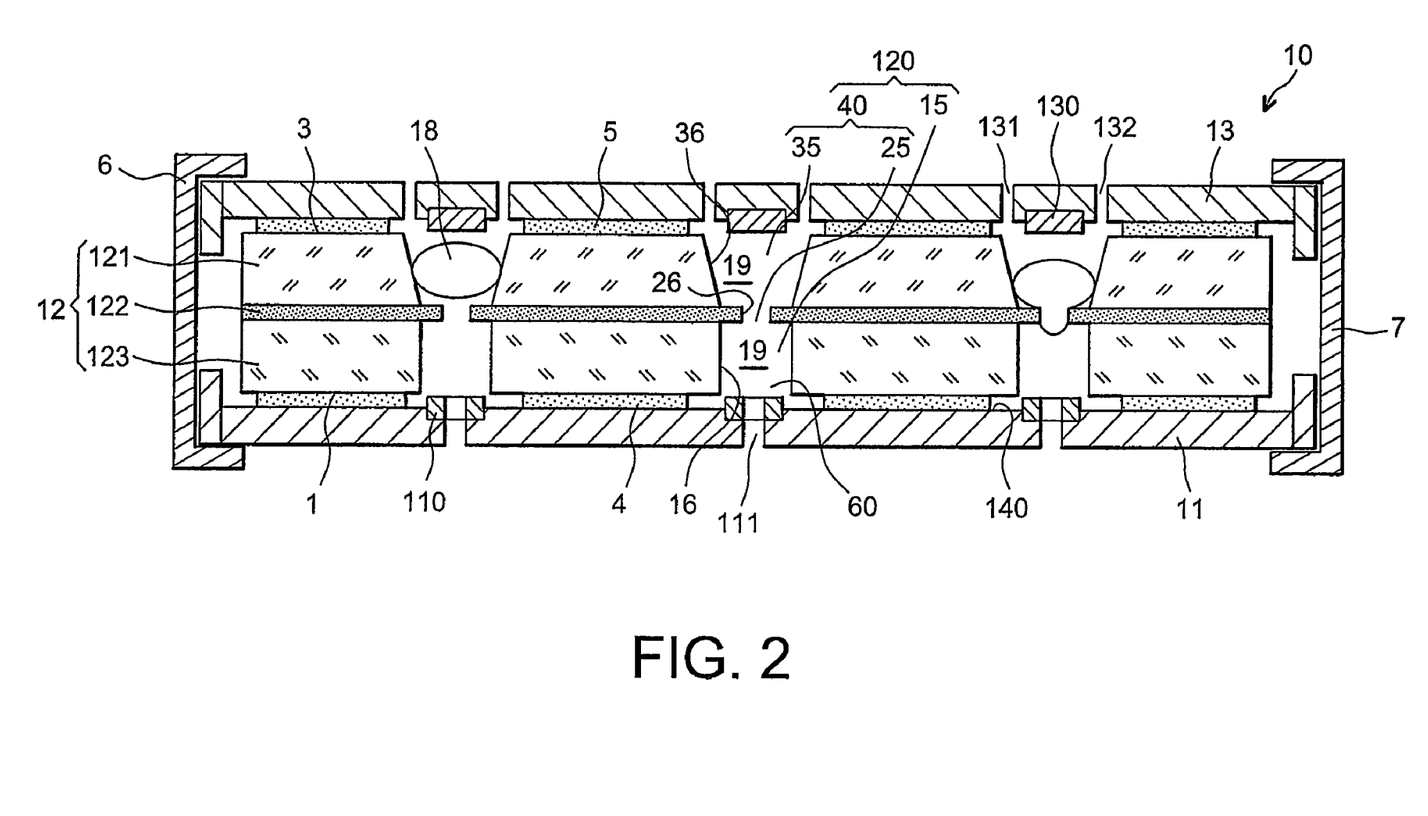
FIG. 2 is a schematic representation of the device in FIG. 1, seen in cross section in the plane P of this FIG. 1.

Referring firstly to FIGS. 1 and 2, these show schematically a device 10 according to the invention in an embodiment designed to allow the electrical activity of nine biological cells to be measured in parallel.

FIG. 1, which is an exploded perspective view, shows the various components of the device 10 before their assembly, while FIG. 2, which corresponds to a section in the plane P of FIG. 1, shows these same components once they have been assembled.

As may be seen in FIGS. 1 and 2, the device 10, which is of square general shape, is composed of seven components that can be assembled in a removable manner, namely:

a first printed circuit 11, which forms the base of this device;

an approximately plane substrate 12 that is placed on top of the printed circuit 11 and has the function of confining the cells 18 by means of through openings 120 in the substrate;

a second printed circuit 13, which is itself placed on top of the substrate 12 and forms the cover of the device 10; this printed circuit, together with the printed circuit 11 and the openings 120 in the substrate 12, defines chambers 19 at the centre of which the cells 18 whose electrical activity it is desired to measure will be placed, one cell per chamber, which chambers are therefore intended to be filled with an extracellular medium or a medium acting as an extracellular medium;

two perforated gaskets 4 and 5 that are inserted between the printed circuit 11 and the substrate 12 in the case of the first one and between this substrate and the printed circuit 13 in the case of the second, which gaskets serve to ensure that the device is sealed, especially between the chambers 19, and to damp the electrical noise and the vibrations emanating from the surrounding medium; and two clamps 6 and 7 whose function is to hold the above components in place in the assembled state.

These seven components correspond to five different modules: thus, the printed circuit 11 corresponds to a first module or module A; the substrate 12 corresponds to a second module or module B; the printed circuit 13 corresponds to a third module or module C; the gaskets 4 and 5 correspond to two examples of a fourth module or module D; whereas the clamps 6 and 7 correspond to two examples of a fifth module or module E.

As shown in FIGS. 1 and 2, the substrate 12 or module B, which represents the centre of the device 10, has nine through openings 120 that are distributed in three rows and three columns.

The openings 120 have two functions, namely, on the one hand, to form microcups 40 capable of confining the cells whose electrical activity it is desired to measure and, on the other hand, to allow the formation, between these cups and these cells, of a seal with a resistance of at least one hundred megaohms and preferably of at least one gigaohm, when a vacuum has been created within the part of the chambers 19 that lie beneath these cups.

In this way, as may be seen in FIG. 2, the substrate 12 is formed from two wafers, 121 and 123 respectively, that are placed on either side of an intermediate membrane 122 which they are fastened to, these wafers and this membrane being recessed in such a way that:

on the one hand, the cups 40 for confining the cells 18 have the shape of funnels, the frustoconical parts 35 of which are delimited by the wall 36 of frustoconical through recesses made in the wafer 121 and the cylindrical parts 25 of which are delimited by the wall 26 of cylindrical through recesses made in the intermediate membrane 122; and on the other hand, the cups 40 communicate with subjacent cylindrical reservoirs 60, having the same axes as the cups, which reservoirs are delimited by the wall 16 of cylindrical through recesses made in the wafer 123 and are capable of housing a volume of liquid medium sufficient to create therein, by suction, the necessary vacuum for obtaining the high-resistance seal.

As may be seen in FIG. 2, which shows, in a very schematic form, a cell before the high-resistance seal has been obtained (the cell on the left) and a cell after the high-resistance seal has been obtained (the cell on the right), the frustoconical part 35 of the cups 40 serve as a receptacle for the cells 18, whereas their cylindrical part 25 serves for producing the high-resistance seal, the latter being, in fact, obtained by deformation of the plasma membrane of said cells and by adhesion of this membrane by invagination against the wall 26 of said cylindrical part.

To give an example, cups whose frustoconical part 35 measures 50 µm at its largest diameter, 30 µm at its smallest diameter and 10 µm in height and whose cylindrical part 25 measures 1.5 µm in diameter and at least 1 µm in height and which sit above a cylindrical reservoir 60 having a diameter of 50 µm for a height of 450 µm, prove to be most particularly suitable for conventional sized cells.

It will consequently be understood that the wafers 121 and 123 of the substrate 12 are preferably made of an easily micromachinable material, particularly silicon, the intermediate membrane 122 then being preferably made of a material having a high dielectric constant, suitable for being micromachined collectively (microtechnology) and of being joined to a silicon wafer by bonding. Such a material is, for example, silicon dioxide ($SiO_2$) or silicon nitride ($Si_3N_4$) when the wafers 121 and 123 are made of silicon.

The printed circuit 11 or module A serves, together with the printed circuit 13 or module C, for applying an electrical voltage to the cells 18 via the liquid medium in which they bathe. The printed circuit 11 also serves to record the variations in this voltage that are induced by a change of state (opening or closing) of the ion channels of said cells.

Thus, the printed circuits 11 and 13, the insulating supports for which may be made in a conventional material of the glass-epoxy type, each carry, on their face opposite the substrate 12, nine electrode contacts 110 and 130 respectively, which are placed so that the axis of each of them is coincident with the axis of the cylindrical part of a cup and are designed to be connected to a circuit for supplying electrical power and for measuring an electrical quantity (which circuit is not shown in FIGS. 1 and 2).

Thus, for example, the electrode contacts 130 of the printed circuit 13 may be connected to a constant potential source, for example earth, whereas the electrode contacts 110 of the printed circuit 11 may be connected both to an electrical generator, via an amplifier, and to an addressing circuit suitable for sequentially collecting the electrical voltage variations recorded by these contacts. This addressing circuit may itself be connected, also via an amplifier, to an apparatus capable of measuring the variation of an electrical quantity, such as a voltmeter or ammeter, and which is connected to the same constant potential source as that to which the electrode contacts 130 of the printed circuit 13 are connected.

The operation of the circuit for supplying electrical power and for measuring an electrical quantity and the analysis of the data collected are, preferably, controlled by a computer system similar to that already used in the patch-clamp field.

Passing through the thickness of the printed circuit 11 are also nine fluid microchannels 111, a few hundred microns in diameter, the function of which is to create, by suction, in the cylindrical reservoirs 60, the vacuum needed to obtain the high-resistance seal. Thus, these channels 111 pass through the electrode contacts 110 and are designed to be connected, at the external face of the printed circuit 11, to capillaries (not shown in FIGS. 1 and 2), which are themselves connected to one or more suction systems such as those conventionally used for sucking a liquid (water pumps, for example).

Also passing through the thickness of the printed circuit 13 are fluid microchannels, a few hundred microns in diameter, but there are eighteen of these distributed as nine channels 131 whose function is to introduce substances into the chambers 19 and nine channels 132 whose function is to remove these substances from said chambers. The channels 131 and 132 may also be used to recirculate the substances into the chambers 19.

In the embodiment of the device according to the invention shown in FIG. 1, the channels 131 and 132 lie on either side of the electrode contacts 130. Like the channels 111, the channels 131 and 132 are designed to be connected to capillaries (not shown in FIGS. 1 and 2) that are themselves connected to one or more liquid delivery systems (microsyringes, micropumps, etc.) and to one or more liquid suction systems or to one or more systems suitable for recirculating the substances into the chambers 19.

Here again, the operation of these various delivery, suction or recirculation systems is preferably controlled by a computer system.

As mentioned above, two gaskets 4 and 5, that correspond to two examples of module D, are inserted between the printed circuit 11 and the substrate 12 in the case of the first gasket, and between this substrate and the printed circuit 13 in the case of the second, for the purpose of sealing the device, especially between the chambers 19, and of damping the electrical noise and the vibrations emanating from the surrounding medium.

To do this, these gaskets are provided with circular perforations, 140 and 150 respectively, that have a diameter slightly greater than both the largest diameter of the cups 40 and the diameter of the cylindrical reservoirs 60, and the axis of which is coincident with the axis of these cups and of these cylindrical reservoirs.

Moreover, these gaskets, which may be only a few microns in thickness, are made of a liquid-impermeable, slightly compressible and possibly flexible material, which is preferably an elastomer like a silicone elastomer, such as a polydimethylsiloxane (PDMS).

Moreover, they are preferably manufactured by moulding so that, on the one hand, they are perfectly matched to the configuration of the substrate 12 and, on the other hand, their manufacturing cost is low enough for them to be able to be replaced with new gaskets each time the device 10 is used.

The clamps 6 and 7, that correspond to two examples of module E, have the function of holding the modules A, B, C and D in place once they have been assembled. Having a U-shaped cross section and a length substantially equal to the edges of the printed circuits 11 and 13, they can be fitted onto the edges of the stack formed by said modules after slight pressure has been applied to this stack.

Figure 3:
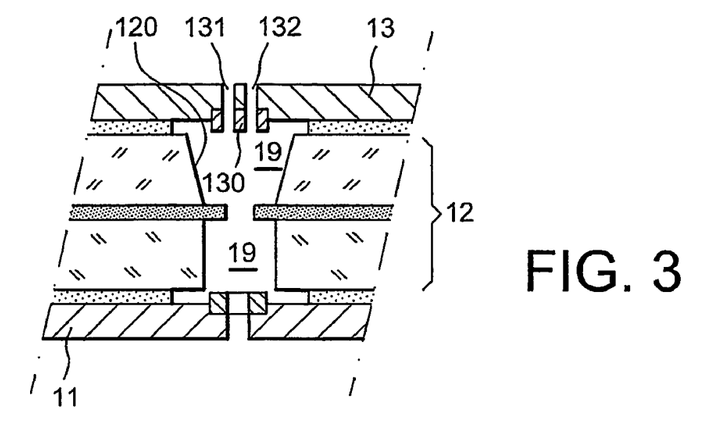
FIGS. 3 to 5 are schematic representations of a portion of a device according to the invention, in a view similar to that in FIG. 2, but for three alternative embodiments of this device.
Figure 4:
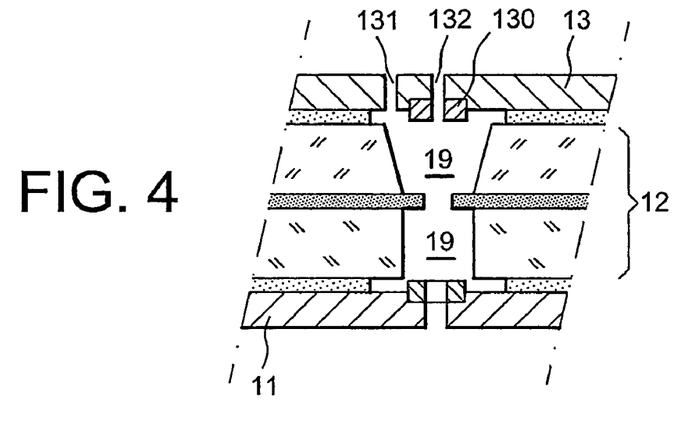
Figure 5:
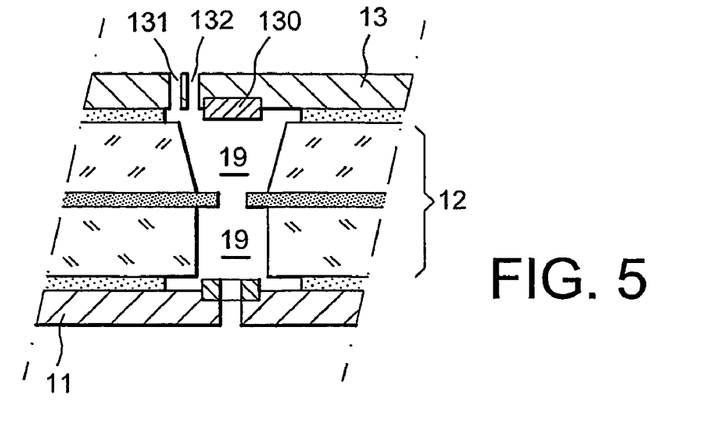

Referring now to FIGS. 3 to 5, these show a portion of a device 10, in three embodiments that differ from one another and from the embodiment shown in FIGS. 1 and 2, by the arrangement of the fluid microchannels 131 and 132.

In the embodiment shown in FIG. 3, the channels 131 and 132 both pass through the electrode contact 130.

In the embodiment shown in FIG. 4, only one of these channels, for example the channel 131, passes through the electrode contact 130, the channel 132 being placed laterally with respect to this electrode contact, whereas in the embodiment shown in FIG. 5 the two channels 131 and 132 are placed laterally and on the same side as said electrode contact.

Figure 6:
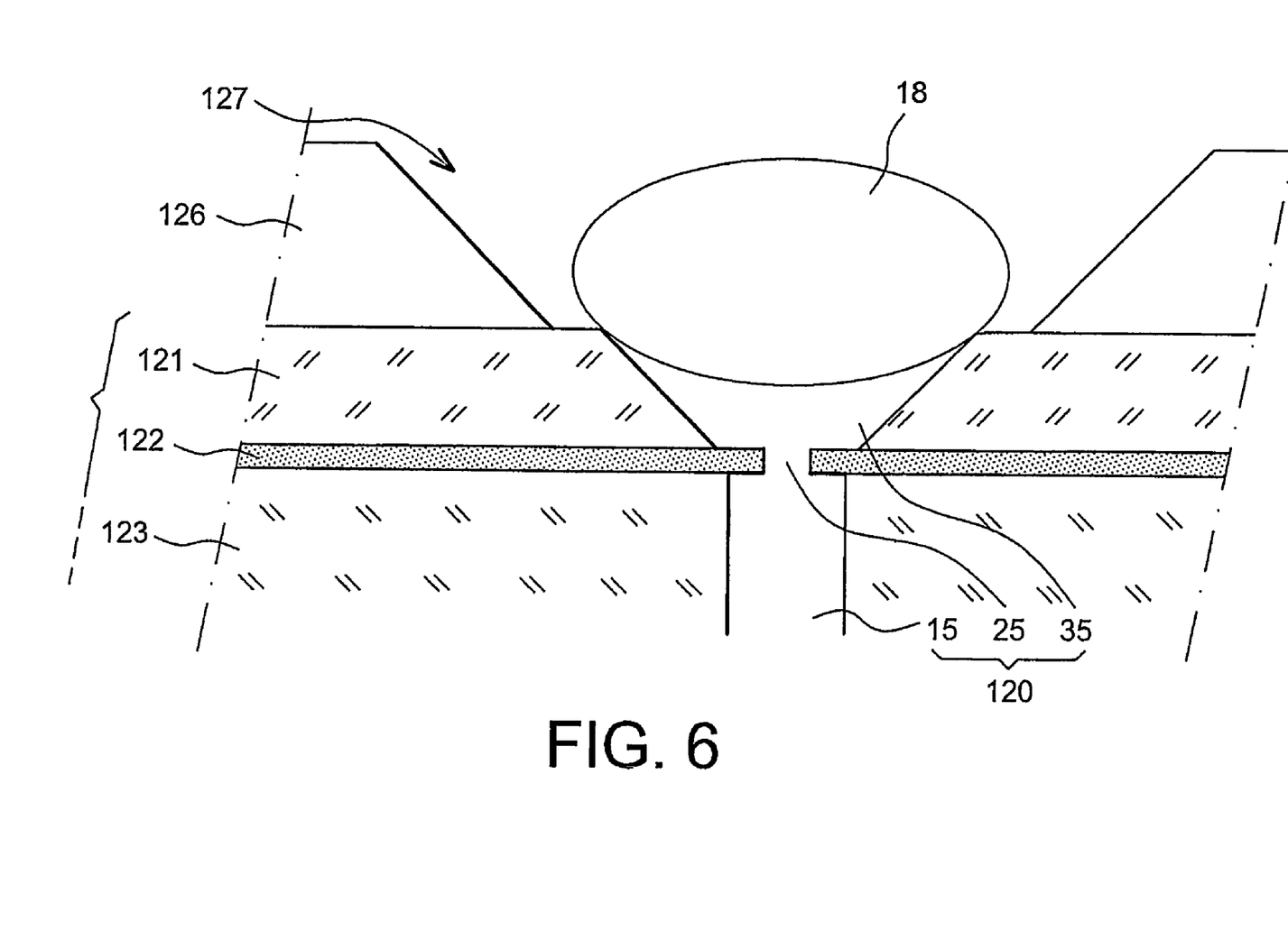
FIG. 6 is a schematic representation of a portion, seen in cross section, of the substrate used in the construction of a device according to the invention, in a first embodiment of this substrate suitable for measuring the electrical activity of large cells.

FIG. 6 shows a portion of a substrate 12 intended to be used in the construction of a device 10, in an embodiment designed to measure the electrical activity of large cells, that is to say cells measuring around 0.7 to 1 mm in diameter.

In this embodiment, the upper face of the substrate 12 is covered with a film 126 which is made of a biocompatible and optionally flexible material, such as a PDMS, a resin or a thermoplastic, and which is provided with through openings 127, coaxial with the openings 120 in the substrate. The dimensions of the openings 127 of the film are such that the cups comprise, in this case, two superposed frustoconical parts, namely a first part, which corresponds to the recesses 35 made in the wafer 121, and a second part, which corresponds to the openings 127 in the film 126.

To give an example, cups:
whose first frustoconical part measures 500 µm at its largest diameter, 300 µm at its smallest diameter and 450 µm in height,
whose second frustoconical part measures 1 mm at its largest diameter, 600 µm at its smallest diameter and 1 mm in height, and
whose cylindrical part measures 1.5 µm in diameter and less than 1 µm in height, have given excellent results.

Here again, it is preferable for the film 126 to be produced by moulding so that its manufacturing cost is low enough for it to be able, like the gaskets 4 and 5, to be replaced with a fresh film each time the device 10 is used.

Figure 7:
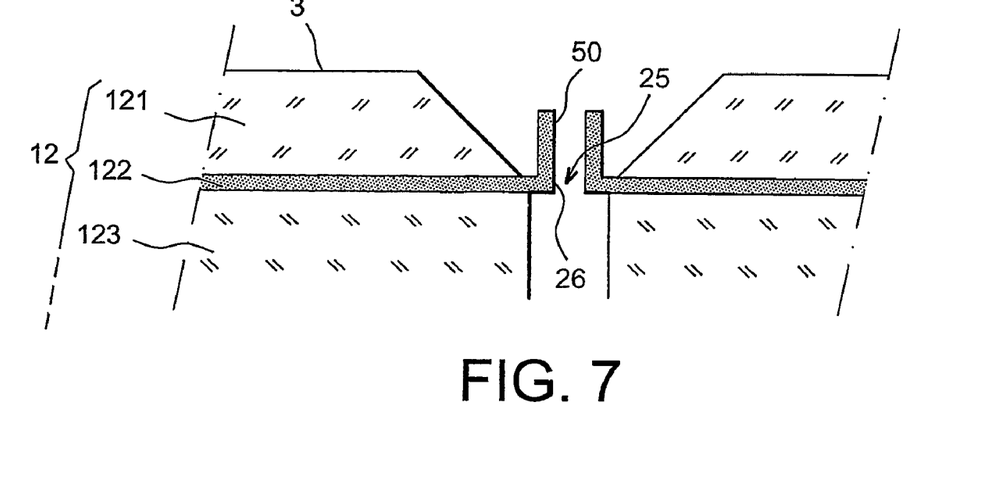
FIGS. 7 and 8 are schematic representations of a portion, seen in cross section, of the substrate used in the construction of a device according to the invention, in two other embodiments of this substrate.
Figure 8:
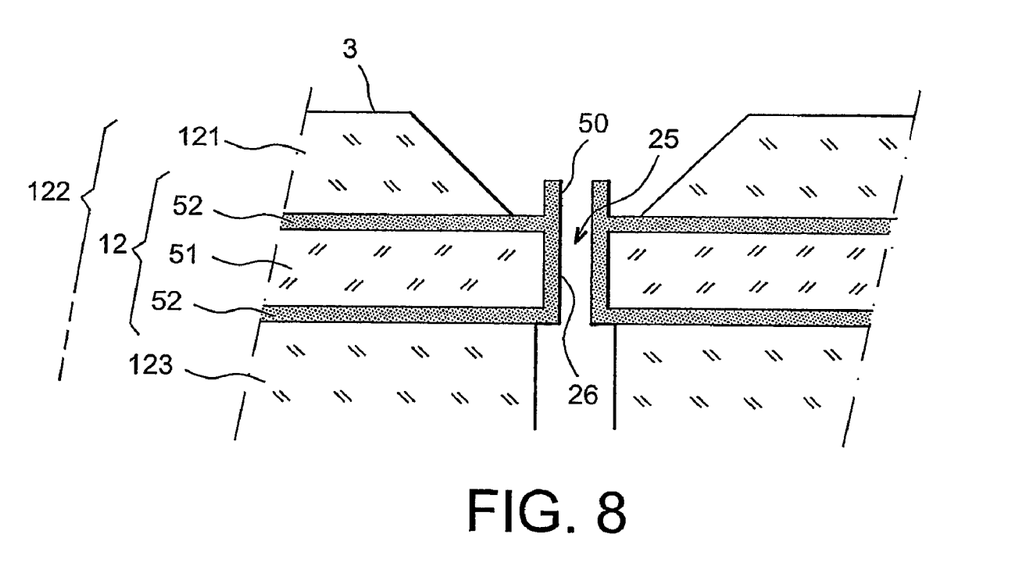

FIGS. 7 and 8 also show a portion of a substrate 12 intended to be used in the construction of a device 10, but in which a cylindrical wall 50 protudes from the wall 26 of each of the cylindrical recesses 25 provided in the intermediate membrane 122 so as to form with the latter a kind of micropipette which extends into the upper part 35 of the openings 120 in the substrate.

In the embodiment shown in FIG. 7, the intermediate membrane 122 is constituted by only one material, preferably a micromachinable material with a high dielectric constant, whereas in the embodiment shown in FIG. 8, the intermediate membrane 122 is strengthened by a silicon wafer and is therefore constituted by a silicon wafer 51 coated on all its faces by a layer 52 of a material with a high dielectric constant.

In both cases, the cylindrical wall 50 is constituted by the same material as the one forming the wall 26 of the cylindrical recesses 25 provided in the intermediate membrane 122.

As an example, when the device 10 is intended to be used for measuring the electrical activity of cells of a conventional size, then substrate 12 as it is shown in FIG. 2 may be based on silicon, for example produced by a process comprising the following steps:

a) preparation of the wafer 123 by:
polishing, on both sides, a first silicon wafer until a thickness of about 450 µm is obtained,
depositing, on both faces of the silicon wafer thus polished, a layer of $SiO_2$,
producing, in the thickness of one of the two $SiO_2$ layer, cylindrical openings approximately 1.5 µm in diameter and
producing, in the thickness of the other $SiO_2$ layer and of the silicon wafer, cylindrical recesses 50 µm in diameter by deep chemical etching, taking measures to ensure that the axis of these recesses is coincident with that of the openings made in the previous step;

b) fastening, by wafer bonding, the wafer 123 thus obtained to a second silicon wafer polished beforehand on both sides, this second wafer being intended to form the future wafer 121;

c) polishing of this second silicon wafer until a thickness of 10 µm is obtained;

d) deposition, on this second silicon wafer, of a layer of $SiO_2$ or $Si_3N_4$; and e) production, in the thickness of the $Si_3N_4$ layer and of the second silicon wafer, of frustoconical recesses.

When the device 10 is intended to be used for measuring the electrical activity of large cells, then the substrate 12 as it is shown on FIGS. 2 and 6 may be based on silicon, for example produced by a process comprising the following steps:

a) preparation of the wafer 123 as described above;

b) preparation of the wafer 121 by:

polishing, on both sides, a second silicon wafer until a thickness of approximately 450 µm is obtained, depositing, on both sides of the silicon wafer thus polished, a layer of $SiO_2$ or $Si_3N_4$, producing, in the thickness of one of the two $SiO_2$ or $Si_3N_4$ layers, cylindrical openings approximately 500 µm in diameter, and producing, starting from these openings, frustoconical recesses in the thickness of the silicon wafer by deep chemical etching;

c) fastening, by wafer bonding, the wafer 121 thus obtained to the wafer 123, and then, optionally;

d) bonding or adhesion by simply pressing a film 126 onto the wafer 121.

The use of the device 10 is extremely simple.

Indeed, after having deposited a module D on a module A, and then a module B matched to the size of the cells whose electrical activity it is desired to measure, on the module D, the cups of the module B are filled with an extracellular medium or a medium that can be used as an extracellular medium, this medium having to be capable of ensuring both conduction of an electrical current and the survival of the cells.

The air present in the cylindrical reservoirs 60 is sucked out by means of the fluid microchannels 111, in order to allow the extracellular medium to flow into these reservoirs. This operation is repeated until the cylindrical reservoirs 60, and then the cups 40, have been completely filled with said extracellular medium.

In the case of large cells measuring around 0.7 to 1 mm in diameter such as xenopus ovocytes, they are deposited in the cups 40, for example by means of a pipette, with one cell per cup, and again suction is applied, via the fluid microchannels 111, in the cylindrical reservoirs 60 in order to obtain a high-resistance seal between each of the cells with the cup in which it is placed and then, possibly, to rupture the plasma membrane fragment thus sealed, if it is desired to work in whole-cell configuration.

Once this seal has been obtained for all the cells, the module B is covered with a module D, then the module D is covered with a module C and, after slight pressure has been applied to the resulting stack of modules A, B, C and D, the modules E are then attached.

In the case of cells of conventional size such as lymphocytes or CHO cells, a suspension of cells, for example containing 105 cells/ml of suspension, is distributed in the whole substrate 12. A suction is applied, via the fluid microchannels 111, in the reservoirs 60 in order to obtain a high-resistance seal between each of the cells with the cup in which it is placed and then, possibly, to rupture the plasma membrane fragment thus sealed. A washing of the substrate 12 allows to remove the cells that are not sealed. The device is closed as previously described.

Then, the device 10 is connected to the circuit for supplying electrical power and for measuring an electrical quantity and the electrical activity of the cells is measured exactly as in the original patch-clamp technique, except that the substances to be tested or detected are introduced into the chambers 19 via the fluid microchannels 131.

When the tests have been completed, the device 10 can be easily dismantled for the purpose of using it again. All that is required is, after the circuit for supplying electrical power and for measuring an electrical quantity has been disconnected, that the modules E be removed so as to be able to separate the modules A, B, C and D from one another. The modules A, B and C may be reused after they have been suitably washed, while the modules D are thrown away to be replaced with fresh modules for subsequent use of said device.

The invention is no way limited to the embodiments that have been described. Thus, for example, the device according to the invention is capable of being adapted to the parallel measurement of the electrical activity of a much larger number of cells, for example 1000 cells, or even more, in which case the substrate 12 is designed to accommodate this number of cells.

Furthermore, the device according to the invention may be coupled to or integrated into other analysis systems such as systems allowing the detection of fluorescence or luminescence signals. In such a case, the printed circuit 13 is made of a transparent material. Such a coupling or integration allows to relate in real time an electrical activity to an ionic signalisation and thus to obtain a response which is at the same time structural and functional, that is to say a dynamic response.

BIBLIOGRAPHIC REFERENCES

[1] HAMILL et al. Pflügers Arch., 1981, 391:85-100
[2] WO-A-96/13721
[3] WO-A-01/25769
[4] WO-A-01/71349
[5] WO-A-99/66329
[6] WO-A-99/31503
[7] WO-A-01/59447
[8] WO-A-00/25121

The invention claimed is:

1. A device for measuring electrical activity of at least one biological element, comprising:

a substantially plane substrate, which has a lower face and an upper face and which has at least one through opening for housing the biological element, said opening being delimited by a set of walls;

two substantially plane plates placed on either side of the lower and upper faces of the substrate and that delimit with the set of walls a chamber that is filled, when the device is being used, with a liquid medium;

wherein each of the plates is provided, on its face lying opposite the substrate, with at least one electrode facing the opening in the substrate;

wherein each of the plates further has at least one channel that starts inside the chamber and connects the chamber to outside of the device; and wherein the chamber communicates with the outside of the device only through the channels.

2. A device according to claim 1, wherein the opening in the substrate comprises an upper part, a central part, and a lower part that are coaxial, the upper and central parts forming a cup for housing the biological element, whereas the lower part forms a reservoir for housing a volume of liquid medium sufficient to create therein, by suction, a vacuum suitable for forming a high-resistance seal between the element and the cup.

3. A device according to claim 2, wherein the upper part of the opening in the substrate is of frustoconical shape, whereas the central part of the opening is of cylindrical shape.

4. A device according to claim 3, wherein the upper part of the opening in the substrate has its largest diameter between 20 and 100 microns and its smallest diameter between 10 and 30 microns and has a height of between 10 and 50 microns, whereas the central part of the opening has a diameter of between 0.1 and 3 microns and a height of 100 microns or less.

5. A device according to claim 3, wherein the upper part of the opening in the substrate has its largest diameter between 500 microns and 1.5 mm and its smallest diameter between 200 and 600 microns and has a height of between 300 microns and 10 mm, whereas the central part of the opening has a diameter of between 0.1 and 3 microns and a height of 100 microns or less.

6. A device according to claim 2, wherein the lower part of the opening in the substrate is cylindrical and measures between 10 and 100 microns in diameter for a height of 300 to 700 microns.

7. A device according to claim 1, wherein the substrate comprises one or more micromachinable materials.

8. A device according to claim 2, wherein the substrate comprises silicon.

9. A device according to claim 1, wherein the substrate is formed from two silicon wafers that are placed on either side of an intermediate membrane to which the two silicon wafers are fastened.

10. A device according to claim 9, wherein the intermediate membrane comprises an insulating material or a silicon wafer coated on its various faces by an insulating material.

11. A device according to claim 10, wherein the insulating material comprises silicon dioxide or silicon nitride.

12. A device according to claim 9, wherein the upper part of the opening in the substrate is delimited by the wall of a through recess made in one of the silicon wafers that are placed on either side of the intermediate membrane, whereas the lower part of the opening of the substrate is delimited by the wall of a through recess made in the other of the silicon wafers.

13. A device according to claim 9, wherein the central part of the opening in the substrate is delimited by the wall of a through recess made in the intermediate membrane.

14. A device according to claim 9, wherein the central part of the opening in the substrate is delimited by a first cylindrical wall corresponding to the wall of a through recess made in the intermediate membrane and by a second cylindrical wall protruding from the first cylindrical wall towards the upper face of the substrate.

15. A device according to claim 2, wherein the upper face of the substrate is covered with a film made of a biocompatible material and is provided with at least one through opening, the opening being coaxial with the upper part of the opening in the substrate, with a same geometry but with a larger cross section.

16. A device according to claim 15, wherein the opening in the film is frustoconical and has its largest diameter between 500 microns and 1.5 mm and its smallest diameter between 200 and 600 microns and has a height of between 300 microns and 1 mm.

17. A device according to claim 1, wherein the plates lying on either side of the lower and upper faces of the substrate comprise an insulating material and the electrodes carried by the plates are plane electrodes, especially Ag/AgCl$^-$ contacts.

18. A device according to claim 1, wherein the plate lying opposite the upper face of the substrate has two channels.

19. A device according to claim 1, wherein the plate lying opposite the lower face of the substrate has only one channel.

20. A device according to claim 18, wherein the two channels of the plate lying opposite the upper face of the substrate pass through the thickness of the plate.

21. A device according to claim 1, wherein the one channel of the plate lying opposite the lower face of the substrate passes through the thickness of the plate.

22. A device according to claim 18, wherein the two channels of the plate lying opposite the upper face of the substrate circulate within the thickness of the plate, substantially parallel to the faces of the plate, until reaching one of edges of the plate.

23. A device according to claim 19, wherein the one channel of the plate lying opposite the lower face of the substrate circulates within the thickness of the plate, substantially parallel to the faces of the plate, until reaching one of edges of the plate.

24. A device according to claim 1, wherein the opening in the substrate, the electrodes carried by the plates lying on either side of the lower and upper faces of the substrate, and the channel of the plate lying opposite the lower face of the substrate are coaxial.

25. A device according to claim 1, further comprising means for sealing the chamber and for damping electrical noise and vibrations emanating from a surrounding medium.

26. A device according to claim 25, wherein the means for sealing the chamber and for damping the electrical noise and the vibrations emanating from the surrounding medium comprises a first gasket inserted between the substrate and the plate lying opposite the lower face of the substrate, and a second gasket inserted between the substrate and the plate lying opposite the upper face of the substrate, each of the first and second gaskets being provided with at least one perforation arranged and dimensioned to circumscribe the electrode on the plate with which it is in contact.

27. A device according to claim 25, wherein the substrate, the plates lying on either side of the lower and upper faces of this substrate, and the means for sealing the chamber and damping the electrical noise and the vibrations emanating from the surrounding medium are modules that are assembled in a removable manner.

28. A device according to claim 27, further comprising means for holding the substrate, the plates that lie on either side of the lower and upper faces of the substrate, and the means for sealing the chamber and damping electrical noise and vibrations emanating from a surrounding medium, in place in an assembled condition.

29. A device according to claim 1, configured for measuring electrical activity of plural biological elements in parallel;
   wherein the substrate comprises a plurality of identical through openings uniformly spaced apart;
   wherein the plates lying on either side of the lower and upper faces of the substrate are printed circuits that are each provided with as many electrodes as the substrate has through openings;

wherein the plate lying opposite the lower face of the substrate has at least as many channels as the substrate has through openings; and wherein the plate lying opposite the upper face of the substrate has at least as many channels for introducing substances and at least as many channels for removing substances as the substrate has through openings.

30. A device according to claim 29, comprising two identical gaskets each provided with as many perforations as the substrate has through openings.

31. A device according to claim 30, comprising two identical clamps that fit over edges of a stack formed by the substrate, the plates lying on either side of the lower and upper faces of the substrate, and the gaskets.

* * * * *